(12) United States Patent
Wolf et al.

(10) Patent No.: US 6,376,233 B1
(45) Date of Patent: Apr. 23, 2002

(54) DEVICE FOR CONDUCTING RESEARCH ON CELL SPECIMENS AND SIMILAR MATERIALS

(75) Inventors: Bernhard Wolf, Stegen; Ulrich Sieben, Reute, both of (DE)

(73) Assignee: Micronas Intermetall GmbH, Freiburg (DE)

( * ) Notice: Subject to any disclaimer, the term of this patent is extended or adjusted under 35 U.S.C. 154(b) by 0 days.

(21) Appl. No.: 09/310,003

(22) Filed: May 11, 1999

Related U.S. Application Data

(63) Continuation of application No. PCT/EP97/05997, filed on Oct. 30, 1997.

(30) Foreign Application Priority Data

Nov. 12, 1996 (DE) ......................... 196 46 505

(51) Int. Cl.[7] ................................. C12M 1/34
(52) U.S. Cl. ............................. 435/288.4; 422/82.02; 324/450; 204/403
(58) Field of Search .................. 435/287.1, 287.2, 435/287.9, 288.4, 288.7, 305.2, 817, 808; 422/82.01–82.11; 204/400, 403; 359/398; 356/246; 324/71.1, 692, 450

(56) References Cited

U.S. PATENT DOCUMENTS

| | | | |
|---|---|---|---|
| 4,072,578 A | | 2/1978 | Cady et al. |
| 4,225,410 A | * | 9/1980 | Pace |
| 4,963,245 A | * | 10/1990 | Weetall |
| 5,187,096 A | * | 2/1993 | Giaever et al. |
| 5,252,294 A | * | 10/1993 | Kroy et al. |
| 5,547,555 A | * | 8/1996 | Schwartz et al. |
| 5,851,489 A | * | 12/1998 | Wolf et al. |

FOREIGN PATENT DOCUMENTS

| | | | |
|---|---|---|---|
| DE | 39 15 920 A1 | | 11/1990 |
| GB | 2 213 269 | * | 8/1990 |
| JP | 57-99188 | * | 6/1982 |
| JP | 62217159 | | 9/1987 |
| WO | WO 87/05624 | | 9/1987 |
| WO | WO 94/03583 | | 2/1994 |
| WO | WO 96/01836 | | 1/1996 |
| WO | 96/31774 | * | 10/1996 |

* cited by examiner

*Primary Examiner*—William H. Beisner
(74) *Attorney, Agent, or Firm*—Akin, Gump, Strauss, Hauer & Feld, L.L.P.

(57) ABSTRACT

A device (1) serves for conducting investigations on cell specimens, wherein the device has a microtiter plate or similar receiving device with a plurality of individual containers for the cell specimens. Furthermore, a measuring facility for recording changes in individual specimens is provided. On the underside the microtiter plate or similar receiving device has a measuring structure which carries at least one sensor allocated to each receiving vessel. The measuring structure can either be combined with a bottomless upper part of a conventional microtiter plate, or instead it is a semiconductor substrate plate (2) with a plurality of bowl-shaped receptacle depressions (3) situated therein and provided as containers. At least one sensor is allocated to each depression.

21 Claims, 4 Drawing Sheets

DEVICE FOR CONDUCTING RESEARCH ON CELL SPECIMENS AND SIMILAR MATERIALS

CROSS REFERENCE TO RELATED APPLICATION

This application is a continuation of International Application PCT/EP97/05997, filed Oct. 30, 1997, the disclosure of which is incorporated herein by reference.

BACKGROUND OF THE INVENTION

The invention relates to a device for conducting research on cell specimens and similar samples, which has a microtiter plate or a similar receptacle device with a plurality of individual containers for cell specimens, and having a measuring device for recording changes in the individual specimens, wherein at least one sensor is provided with each receptacle container.

Various medical-biochemical test procedures can be conducted with the aid of so-called microtiter plates. Microtiter plates have a plurality of receptacle tubes arranged alongside one another, into which the cell specimens, for example a suspension of metastatic cells, are introduced. Subsequently, an indicator solution, for example a fluorescent dye, is added. To study whether certain substances can influence the metastatic cells, especially kill them, various cytotoxic substances are added. The introduction of cell specimens, indicator solution and medications takes place in a sampling technique conducted by means of an automatic device. Cell changes can be detected in a fluoroscopic procedure or with the aid of a spectrometer.

Besides chemotherapy testing, microtiter plates can also be studied for research on cancer cells as to their metastatic tendency. In this case, a test substrate consisting of a layer of cells or embryonal HM-cell cultures or a collagen matrix, is positioned in the containers upon which the metastasic cells are then placed. According to the degree of change, a measure for the invasion index or the metastatic index can be derived. This procedure, in which biological layers of another substance are more or less influenced, is also called biocorrosion. Studies, for example of plastics for biocompatibility, are also possible therewith. That is, it is studied whether or not cells penetrate into the plastic under investigation.

With these various studies, a fluoroscopy process is usually provided for the evaluation, with measurement assessment by a microplate reader or by means of a spectrometer. Consequently, on the one hand, a not inconsiderable equipment expenditure is necessary for the functional suitability of the overall device, and on the other hand, the measurement assessments do not in all cases provide information to the extent desired, for example even about the running reaction process. It is furthermore disadvantageous that with commercially available microtiter plates, comparatively large sample amounts are necessary. Appropriate sample amounts, however, are not always available, for example of biopsy material.

A device is known from German published patent application DE 39 15 920 A, which has a micromechanical structure with a plurality of depressions situated in a block of semiconductor material as sample containers The sample containers are installed in the block through chemical etching. These receptacles are nonetheless suited only for very small sample amounts. Moreover, special sampling facilities are necessary.

A microelectronic device is known from published International (PCT) application WO-A-9601836, which likewise has a plurality of individual containers as sample containers, which as microcontainers are suited exclusively for accommodating the smallest sample amounts. The electrodes provided in the microcontainers can basically only be used for conductivity measurements. This device is equipped for DNA examination, and among others, no physiological measurements on living cells can be conducted with it.

SUMMARY OF THE INVENTION

An object of the present invention is to create a device of the type mentioned at the beginning which makes possible a plurality of different examinations at a reduced overall cost, including continuous monitoring of a reaction process, and which is also simpler to handle.

For accomplishing this objective, it is proposed in accordance with the invention that the measurement facility has semiconductor sensors with at least one interdigital condenser situated on one or more substrate plates, and that a honeycomb-like tube structure consisting of a bottomless upper part of a commercially available microtiter plate is mounted on the semiconductor substrate plate and tightly connected with the substrate plate.

By using a microtiter plate "upper part," the facilities previously used in connection with microtiter plates, especially the automatic sampling machine, can continue to be used. Moreover, correspondingly more test fluid can be accommodated according to need. Semiconductor sensors offer a plurality of different measuring possibilities so that appropriate sensors can be provided according to the application and measuring object. Such sensors can also be realized in the smallest designs, so that it is correspondingly possible to work with even the smallest sample amounts. Thus, studies on cells, for example, are also still possible even if these can only be taken from a patient in a very small amount, for example as biopsy material. It is also advantageous that the receptacle device with the individual containers and the practically integral measuring facility form a complete functional unit and also a compact construction unit, which is also simpler to handle. The sensors are hereby respectively part of the measuring chamber, so that these no longer need to be brought into connection with a separate measurement facility for evaluation. Also advantageous is that a measurement during a running reaction process, and moreover measurement simultaneously with all individual containers, is possible.

With the aid of interdigital condensers as sensors, measurements of changes in shape of the cells can in particular be conducted, and furthermore, impedance and capacitance changes of the cell membrane can be measured. Antibodies which accumulate on cells can also be detected, since they change the dielectric constants in the area of the interdigital structure. Preferably the electrodes of the interdigital condensers intermesh in pairs with one another.

Expediently, several, preferably different sized, interdigital condensers are provided. These have a distinct sensitivity, so that accordingly a larger measuring area is covered, and a higher resolution in the individual measurement areas is made possible.

Preferably, it is provided that the sensors, at least for some receptacles, are situated on a common wafer-like semiconductor substrate plate. On such a semiconductor substrate plate, a plurality of sensors can be accommodated by known manufacturing technology in a narrow space, so that a precondition for an especially compact design of the device is thereby present. The semiconductor substrate plate with the individual sensors hereby practically forms a measurement structure allocated to the receptacles.

A preferred embodiment provides that the device have at least one semiconductor substrate plate with a plurality of small bowl-shaped receiving depressions situated within it as containers, and that the sensors allocated to the depressions, overall forming a measurement structure, be a component of the substrate plate.

It is also possible with this device, in particular, to work with the smallest sample amounts. Moreover, such a device can be manufactured completely with semiconductor technology. Furthermore, an extremely compact construction is realizable therewith.

According to a refinement of the invention, there can also be provided herein, in the area of an individual container or a receptacle depression, several, preferably different, sensors, in particular as a sensor array, so that different parameters can be recorded simultaneously during the examination. Such a sensor array can be manufactured especially economically as an integrated circuit, and makes possible the measurement of different chemical or biological substances on the most constricted space.

Depending on the object of the investigation, there also exists the possibility, however, of arranging different sensors with the individual receptacles, wherein one or more receptacles have the same sensors in their respective area and different types of sensors are provided with other receptacles or groups of receptacles.

The measurement facility with its measuring structure is expediently arranged on the underside of the receptacle device, and each receptacle carries at least one sensor in the floor and/or in the side wall. Preferably, the sensor(s) is(are) integrated into the measurement structure on the floor of the receiving device, but sensors can also be provided on or in the side walls of the receiving vessel. For example, conductivity sensors can be arranged on the side walls.

With studies on living cells by means of microtiter plates, a tempering to guarantee the normal living conditions of the cells is problematic. Under certain conditions, moreover, there exists the danger that the cells to be examined can die off on account of lower temperatures, so that the measuring result can then be considerably distorted. In order to avoid this, it is proposed in a refinement of the invention that the microtiter plate or the like have a tempering device on the underside, preferably underneath the measuring structure, which is preferably thermostatically regulable. Exact temperature specifications can thereby be maintained, and studies on thermally sensitive measurement objects are also possible therewith.

In order to be able to record the temperature near the measuring point, at least one temperature measuring sensor, especially a temperature measuring diode, is arranged on the substrate having the measuring structure. In manufacturing the measuring structure, such a temperature measuring sensor, optionally provided at each receptacle, can be produced along with it and thereby be integrated into the measuring structure.

Optionally, the wall thickness of the substrate plate having the sensors and optionally the tempering facility and the like can be,reduced in the area of the individual containers and be dimensioned for a fluoroscopy measurement process. Here, there also exists the possibility for the substrate plate to have at least one transilluminable channel in the area of the individual containers. It is optionally also possible thereby to operate with the previously used fluoroscopy technique, in addition to electrical or electronic measurement.

It is especially beneficial if the semiconductor substrate plate as the measurement structure has at least one field effect transistor, especially an ISFET, whose gate is exposed for contact with the cells. By the direct contact of the gate forming an electrode, a high measurement sensitivity exists. It is advantageous if, in at least one insulated intermediate area of the electrode of the interdigital condenser, an electrochemical-sensitive layer is provided. The sensor is then better suited for detecting certain physiological substances eliminated by the cells, for example oxygen or complex gases. For this, electroactive substances can be placed in the intermediate spaces or be packed in ceramic sponges.

In another embodiment, fiber optics are provided between the electrodes of the interdigital condenser, and for receiving and detecting the light running through the respective fiber optics, light detectors are arranged in the substrate. The measurement facility then makes available additional information, for example about scattered light emitted by the cells, which makes possible an inference on the vitality of the cells. Advantageously, a self test of the measuring facility can consequently be conducted with the aid of the light detectors.

A more exact monitoring of the cells standing in contact with the measurement structures is made possible if CCD sensors, especially in the form of a CCD line or a CCD array, are incorporated into the substrate. An even higher resolution is thereby attained with optical measurement, so that it is also possible, in particular, to monitor morphological changes of individual or several cells arranged in specific areas of the measurement structure.

Expediently, the measurement outputs of the sensors arranged on a common substrate are connected with a control and evaluation facility, in particular integrated on the substrate and in particular connected through a conductor matrix or a network. In the integrated control and evaluation facility, for example, a preprocessing of the measurement values can be undertaken. The evaluation electronics also permits a material and function-specific training of the sensor.

Such an embodiment of the device of the invention can (with appropriate construction of the control and evaluation facility) practically be constructed as an ASIC for microtiter plates, which is adaptable to the most varied measurement objectives and evaluation procedures.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

DETAILED DESCRIPTION OF THE INVENTION

Figure 1:
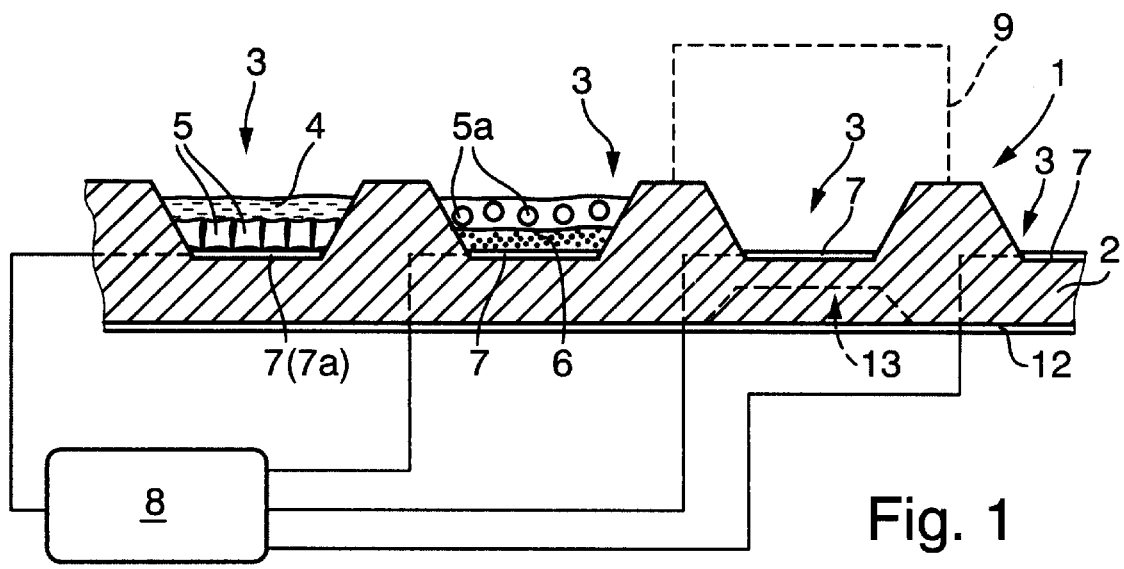
FIG. 1 is a partial sectional view of a device of the invention in longitudinal representation.

A partial area of a device 1 for conducting tests on cell specimens is shown in FIG. 1 in longitudinal section. In this embodiment, a semiconductor substrate plate 2 is provided with a plurality of bowl-shaped receptacle depressions 3 situated in it, which serve as containers for accommodating cell specimens. For clarification, in two receptacle depressions 3 situated alongside each other, various filler media for different tests are represented. In the left depression, cells 5 are situated in a reagent 4, and a chemotherapy test can hereby be conducted. In the adjacent receptacle depression 3 a test substrate 6 is situated consisting of a cell layer or embryonal HM cell cultures or a collagen matrix, on which a suspension with metastastic cells is found. A metastasic index is determined with this.

In order to be able to establish changes on the cells 5 or the test substrate 6, sensors 7 are arranged in the floor area of the depressions 3. As sensors 7, individual sensors but preferably several different sensors 7, can be provided as a sensor array 7a. Field effect transistors, interdigital condensers or similar semiconductor structures, on the other hand also optical sensors, especially surface wave guides, grating couplers and the like come into consideration. As indicated in FIG. 1, the sensors 7 are connected with a control and evaluation facility 8. Optionally, this control and evaluation facility can be wholly or partially integrated on the semiconductor substrate plate 2.

Moreover, there exists the possibility of arranging the control and evaluation facility 8 on the reverse side of the semiconductor substrate plate 2 facing away from the sensor structure and of connecting it through interlayer connections with the sensor terminals. An especially compact construction is thereby possible.

For example, the control and evaluation facility 8 can include a multiplexer, an AD/DA transducer with sensor control, a microprocessor, as well as an IO unit. Consequently, a complete research device is created with which measurements can be continuously conducted during reaction processes.

Besides the sensors 7, stimulus electrodes or the like can also be provided to stimulate the cells to be examined and, for example, to induce the spontaneous emission of a substance to be detected with the sensors.

It is advantageous for the most varied measurements, if for each receptacle depression 3 a double phantom circuit with four field effect transistors, two interdigital condensers and two oxygen indicators is preferably provided on a sensor array 7a.

The embodiment of a device 1 of the invention, depicted in FIG. 1, can be constructed extremely compactly and is especially suited for investigations on very small sample amounts.

As indicated in dotted lines in FIG. 1 on another receptacle depression 3, fixtures 9 projecting above the substrate plate 2 can be provided to enlarge the volume accommodated by the depressions 3.

Figure 2:
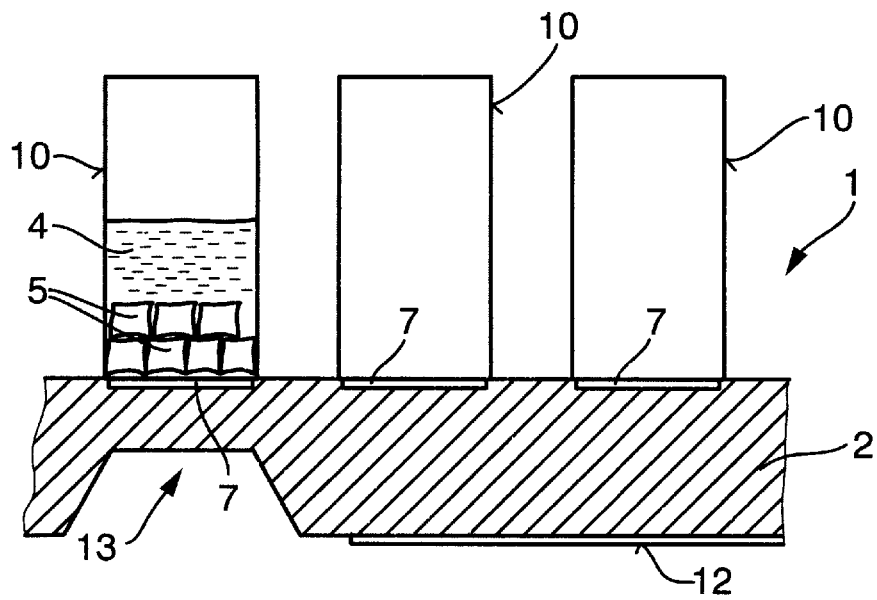
FIG. 2 illustrates a device of the invention in a somewhat modified form relative to FIG. 1, likewise in a longitudinal view, partially in section.
Figure 3:
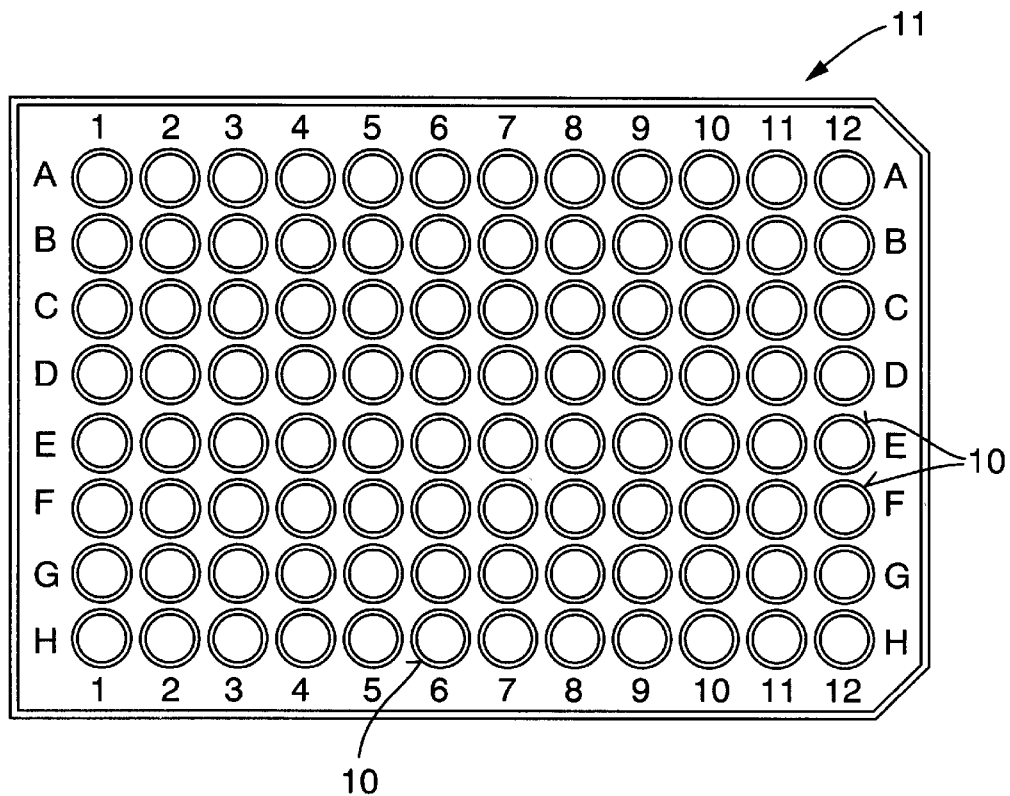
FIG. 3 is a plan view of a receptacle device with a plurality of individual containers.

FIG. 2 shows an embodiment with small tube-shaped individual containers 10, which are installed on a semiconductor substrate plate 2. Sensors 7 are also situated here in the floor area of each individual container 10.

FIGS. 3 to 6 show in various views the essential parts of a device 1 of the invention. In the embodiment represented here, for the containers 10 of a commercially available microtiter plate 11, the floor area is divided (FIG. 3) so that small tubes result throughout. This microtiter plate upper part 11a (FIG. 5) is then set upon the substrate plate 2 (FIG. 4) and firmly joined to this, preferably by ultrasound welding. The substrate plate 2 with its respective sensors then forms the floor of the individual containers 10. The sensors or sensor arrays on the substrate plate are arranged at the spacing of the individual tubes or individual containers when using a microtiter plate.

By using a microtiter plate upper part 11a for constructing the receptacles, there exists the possibility of being able to use unaltered apparatus previously utilized in connection with commercially available microtiter plates, for example an automatic sampling device, a microplate reader and the like.

Figure 4:
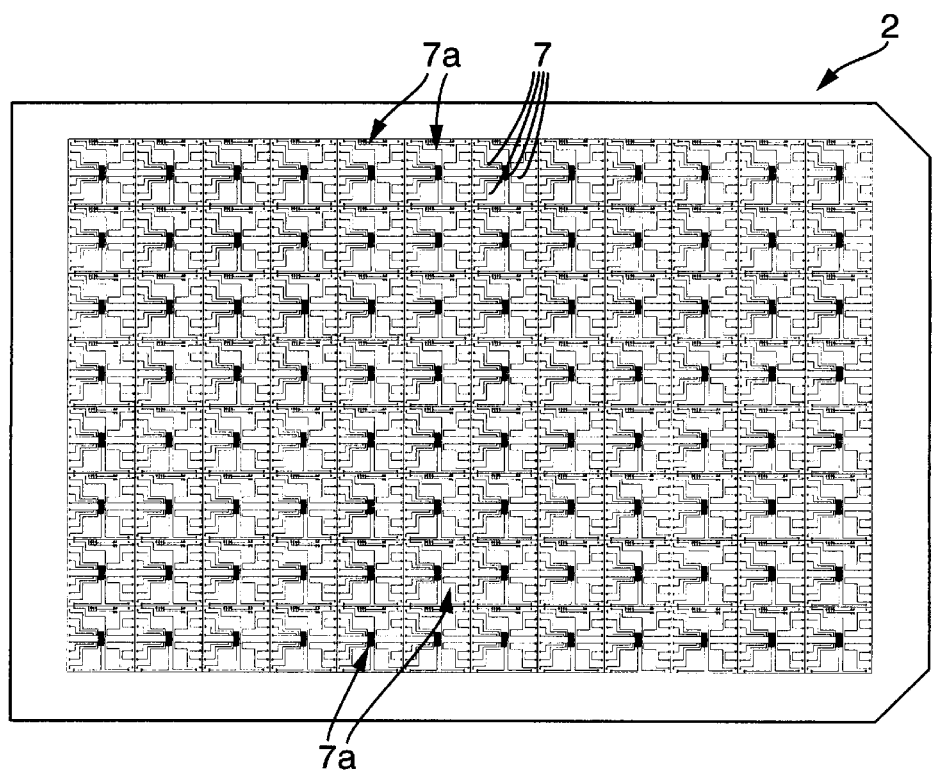
FIG. 4 is a plan view of a wafer-like semiconductor substrate plate with a plurality of sensors.
Figure 5:
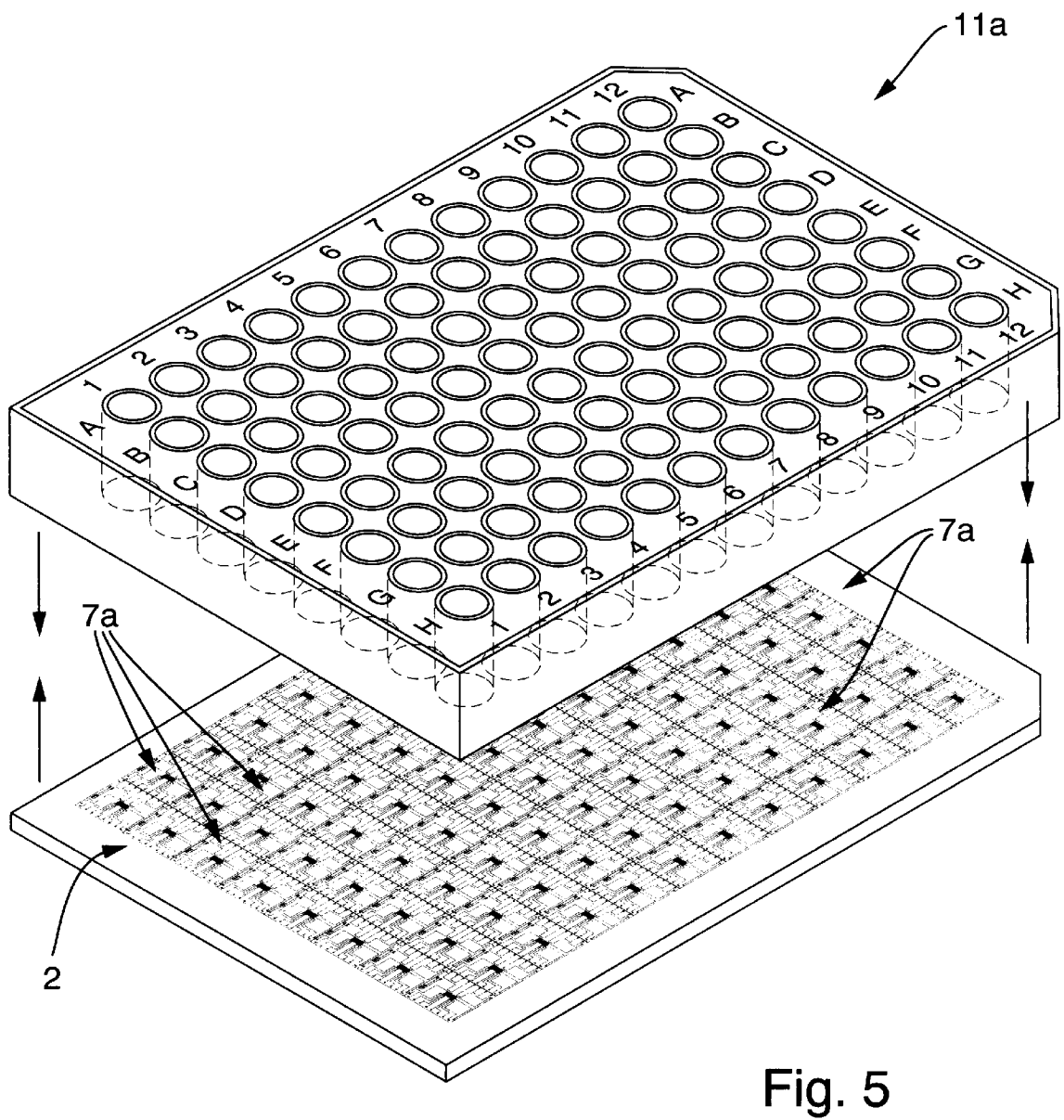
FIG. 5 depicts the elements shown in FIGS. 3 and 4 prior to assembly.
Figure 6:
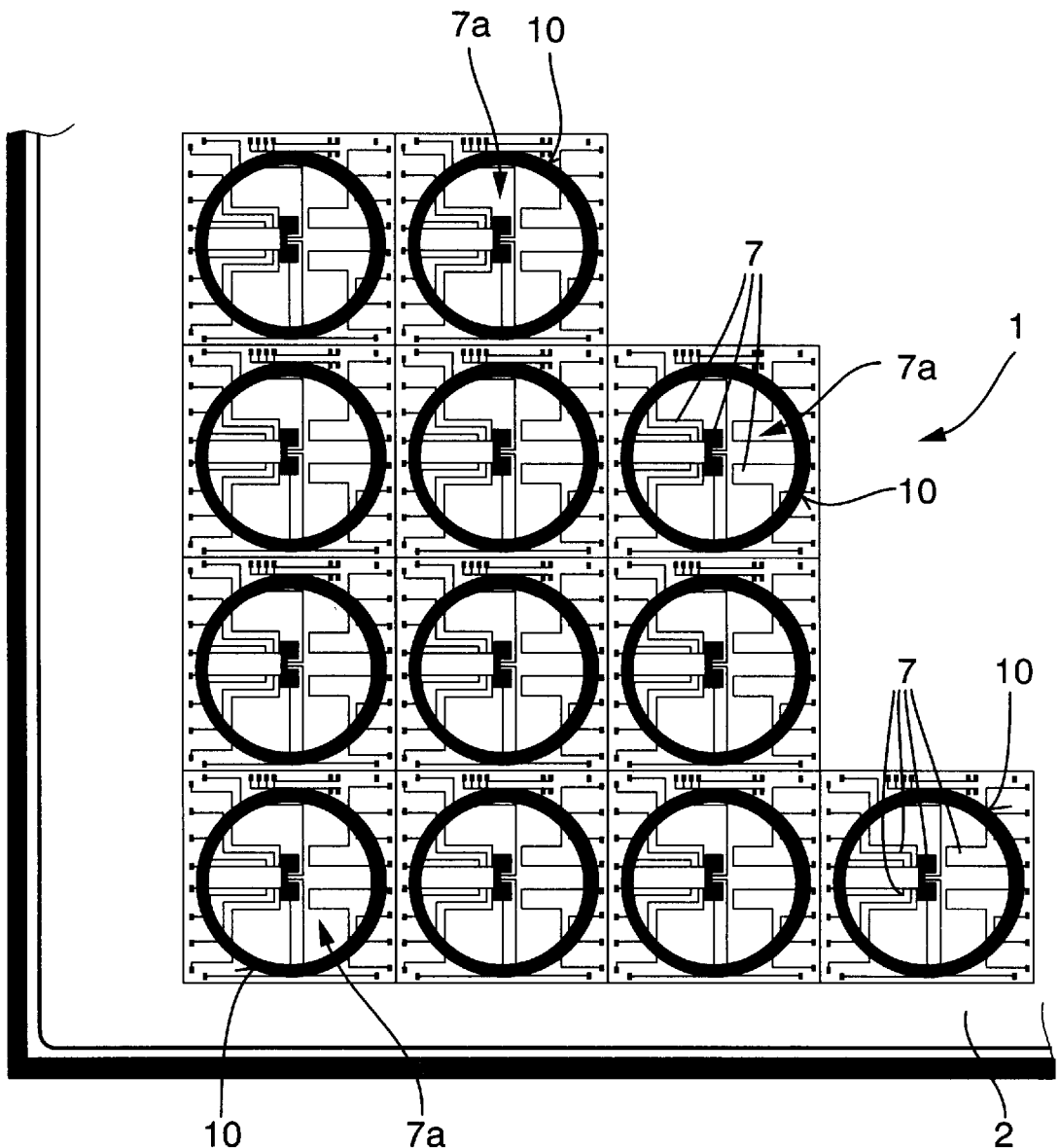
FIG. 6 is a detail sectional representation of a device of the invention in plan view.

As is recognizable from FIGS. 4 and 5 and especially FIG. 6, the sensors 7 are formed by sensor arrays 7a with several different individual sensors. As already mentioned previously, parts or the entire control and evaluation facility 8 can also be situated on the substrate plate. The connection leads to the junctures lying outside the measuring chambers of the respective sensor arrays 7a allocated to an individual container 10 are not represented for the sake of simplicity. FIG. 6 shows in an enlarged plan view a series of sensor arrays 7a with containers 10 arranged alongside one another.

Besides electronic sensors on a semiconductor basis, other sensors, for example on an optical basis, or biological sensors, can be provided and used, preferably in combination with the previously described sensors.

In the embodiments in accordance with FIGS. 1 and 2, a heating layer 12 is provided on the underside of the semiconductor substrate plate 2, by means of which a tempering of the substrate plate, and thereby also of the specimens found in the receptacle depressions 3, is possible. With cell specimens their normal living conditions can also be created with respect to temperature, so that studies over a longer period of time are possible. There also exists the possibility of providing partial, separated segments of heating layers, instead of a continuous heating layer 12, so as to be able to generate different temperatures in certain regions as needed.

For thermostatic regulation of the heating, temperature measuring sensors can be provided at one or more sites on the substrate plate. Such temperature measuring sensors can also be integrated directly in the sensors 7 allocated to the individual receptacle depressions or similar individual containers. Temperature measuring sensors in the area of the individual containers can also be used for recording the biological activity of the cells, in addition to thermostatic regulation of a heating system.

In FIGS. 1 and 2, recesses 13 are provided in the substrate plate 2 on the underside on two depressions or individual containers, and the wall thickness of the substrate is thereby reduced to the extent that it is also possible to operate here (additionally) with a fluoroscopy measuring procedure.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. A device for conducting studies on cell specimens and similar samples, comprising a receiving device with a plurality of individual containers for cell specimens and a measuring facility for recording changes in specimens received in the individual containers, wherein at least one sensor (7) is provided for each individual container (3, 10), wherein the measuring facility comprises semiconductor sensors (7) situated on at least one substrate plate at least with an interdigital condenser, and wherein the individual containers are arranged in a honeycomb-configured small tube structure, comprising a bottomless upper part (11a) of a conventional microtiter plate, which is set upon and tightly connected to the substrate plate (2).

2. The device according to claim 1, wherein the sensors for at least some of the containers are situated on a common wafer-shaped semiconductor substrate plate (2).

3. The device according to claim 1, wherein different sensors are arranged with the individual containers.

4. The device according to claim 1, wherein the measuring facility is arranged with a measuring structure on an underside of the receiving device, and each individual container (3, 10) carries at least one sensor (7) on its floor and/or on its side wall.

5. The device according to claim 1, wherein the microtiter plate has a tempering device (12) on its underside, beneath the substrate plate(s) or measuring structure, which is thermostatically regulable.

6. The device according to claim 1, wherein the substrate plate (2) is a semiconductor plate tightly connected with the upper part (11a) of the microtiter plate by ultrasonic welding.

7. The device according to claim 1, wherein a wall thickness of the substrate plate having the sensors (7) is reduced in an area of the individual containers and dimensioned for a fluoroscopy measurement process.

8. The device according to claim 7, wherein the substrate plate has at least one transilluminable channel in the area of the individual containers.

9. The device according to claim 1, wherein in an area of an individual container (3,10) more than one different sensors (7) are provided as a sensor array.

10. The device according to claim 1, wherein the substrate plate is a semiconductor substrate plate (2) having as a measuring structure at least one field effect transistor, a gate of which lies exposed for contact with the cells.

11. The device according to claim 10, wherein the at least one field effect transistor comprises an ISFET.

12. The device according to claim 1, wherein the interdigital condenser provided as sensor (7) has electrodes intermeshing with one another in pairs.

13. The device according to claim 12, wherein several interdigital condensers of different size are provided.

14. The device according to claim 12, wherein in at least one insulated intermediate space of the electrodes of the interdigital condenser, an electrochemical-sensitive layer is provided.

15. The device according to claim 12, wherein between the electrodes of the interdigital condenser, fiber optics are provided, and wherein light detectors for recording and detecting light running through the respective fiber optic are arranged in the substrate.

16. The device according to claim 1, wherein CCD sensors, in the form of a CCD line or a CCD array, are incorporated into the substrate.

17. The device according to claim 16, wherein the substrate (2) has a measuring structure having at least one temperature measuring sensor in a form of a temperature measuring diode arranged thereon.

18. The device according to claim 1, wherein a multiplexer, an AD/DA transducer with sensor control, a microprocessor, and an IO unit are situated on the substrate plate (2) as a control and evaluation facility (8).

19. The device according to claim 1, wherein as sensors (7) optical sensors, surface wave guides, or grating couplers are provided.

20. The device according to claim 1, wherein the sensors allocated to the individual containers are connected by a conductor matrix or network with a control and evaluation facility (8) which is optionally arranged together with the sensors on a common substrate plate (2).

21. A device for conducting studies on cell specimens and similar samples, comprising a receiving device with a plurality of individual containers for cell specimens and a measuring facility for recording changes in specimens received in the individual containers, wherein at least one sensor (7) is provided for each individual container (3), wherein the measuring facility comprises semiconductor sensors (7) situated on at least one substrate plate at least with an interdigital condenser, wherein the substrate plate(s) is a semiconductor substrate plate (2) with a plurality of small bowl-shaped receptacle depressions (3) situated therein as the individual containers, and wherein the measuring facility comprises a measuring structure with sensor (s) (7) respectively allocated to each depression (3), the measuring structure being a component of the substrate plate (2).

* * * * *